US005391547A

United States Patent [19]
Cole et al.

[11] Patent Number: 5,391,547
[45] Date of Patent: Feb. 21, 1995

[54] METHOD USING 5,10,15,20-TETRAKIS(4-CARBOXYPHENYL)-PORPHINE FOR TREATING CANCERS OF THE LUNG

[75] Inventors: Dean A. Cole, Germantown, Md.; David C. Moody, III, Superior, Colo.; L. Edward Ellinwood, Grand Junction, Colo.; M. Gerard Klein, Grand Junction, Colo.

[73] Assignee: University of California Office of Technology Transfer, Alameda, Calif.

[21] Appl. No.: 914,376

[22] Filed: Jul. 15, 1992

Related U.S. Application Data

[62] Division of Ser. No. 539,999, Jun. 15, 1990, Pat. No. 5,162,231.

[51] Int. Cl.⁶ ............... A61K 31/555; A61K 43/00
[52] U.S. Cl. ................................. 514/184; 424/1.13; 424/1.65
[58] Field of Search ............... 514/184; 424/1.13, 1.65

[56] References Cited
PUBLICATIONS

D. A. Cortese et al., "Hematoporphyrin Derivative in the Detection and Localization of Radiographically Occult Lung Cancer," Am. Rev. Respir. Dis. 126, 1087 (1982).
H. Kato et al., "Early Detection of Lung Cancer by Means of Hematoporphyrin Derivative Fluorescence and Laser Photoradiation," Clin. Chest Med. 6, 237 (1985).
K. B. Patel et al., "Fluorescing Cells In Sputum After Parenteral HPD," *Progress in Clinical and Biological Research*, vol. 170. D. Doiron and C. Gomer, Eds.; Porphyrin Localization and Treatment of Tumors, 521 (1984).
J. A. Mercer-Smith et al., "The Development of Copper-67-Labeled Porphyrin-Antibody Conjugates," *Targeted Diagnosis and Therapy*, vol. 1, Antibody-Mediated Delivery Systems; J. D. Rodwell, Ed. (Marcel-Dekker), New York, 1988 pp. 317-352.
J. C. Roberts et al., "Preparation and Characterization of Copper-67 Porphyrin-Antibody Conjugates," J. Immunol. Methods 105, 153 (1987).
G. Firnau et al. "⁶⁴Cu Labelling of Hematoporphyrin Derivative for Noninvasive In-Vivo Measurements of Tumor Uptake," *Progress in Clinical and Biological Research*, vol. 170, D. Doiron and C. Gomer, Eds; Porphyrin Localization and Treatment of Tumors, pp. 629-636 (1984).

*Primary Examiner*—Jerome D. Goldberg
*Attorney, Agent, or Firm*—Samuel M. Freund

[57] ABSTRACT

Method using tetra-aryl porphyrins for and, in particular, 5,10,15,20-tetrakis(4-carboxyphenyl)porphine as a fluorescent tracer for cancers of the lung, and as a radiotracer therefor as a complex with $^{67}$Cu. The latter complex also provides a source of beta radiation for selective destruction of lung malignancies as well as gamma radiation useful for image analysis of the situs thereof by single photon emission computed tomography, as an example, both in vivo. Copper-64 may be substituted for the $^{67}$Cu if only radiotracer characteristics are of interest. This lighter isotope of copper is a positron emitter, and positron emission tomography techniques can be used to locate the malignant tissue mass.

2 Claims, 1 Drawing Sheet

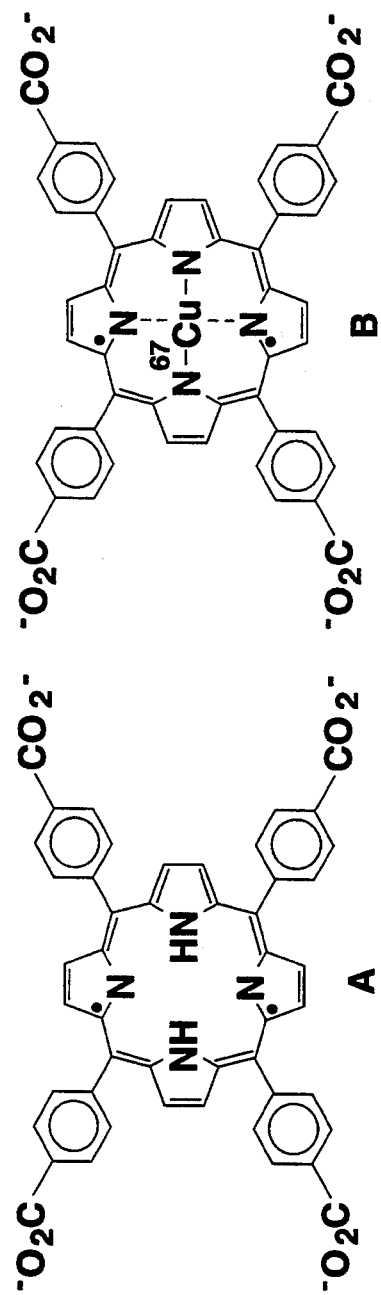
Figure

METHOD USING 5,10,15,20-TETRAKIS(4-CARBOXYPHENYL)PORPHINE FOR TREATING CANCERS OF THE LUNG

This is a divisional of application(s) Ser. No. 07/539,999, filed on Jun. 15, 1990, now U.S. Pat. No. 5,162,231.

BACKGROUND OF THE INVENTION

The present invention relates generally to the use of porphyrins to detect lung cancer, and more particularly to the use of tetra-aryl porphyrins, of which 5,10,15,20-tetrakis(4-carboxyphenyl)porphine is an example, to detect and treat lung cancer. This invention is the result of Contract No. W-7405-ENG-36 between the Regents of the University of California and the U.S. Department of Energy.

Cancer of the lung is a major world health problem and remains untreatable. It has been determined that in 1986 malignant lesions of the lung killed more than three times as many men as cancer of the colon and surpassed breast cancer as the major lethal malignant disease in women. Despite an enormous commitment of resources during the past decade, the success in the management of lung cancer has been minimal at best. In fact, in 1988, the annual death rate for lung cancer in the United States was estimated to approach 110,000 deaths. In addition, 150,000 new cases of lung cancer were diagnosed in 1988, making lung cancer the number one cancer killer. Attempts at mass-screening high risk populations have also been unsuccessful.

The treatment of lung cancer has largely been unsuccessful and at times controversial. The overall five-year survival for a patient with lung cancer still remains less than 10%. The practice of surgically resecting the tumor is the most successful of all treatments; however, in most cases the malignant lesions recur or metastasize. The use of radiotherapy and chemotherapy have also had limited success in prolonging the life of lung cancer patients. In fact, the median survival for a patient with small cell lung carcinoma, who is treated with chemotherapy and with or without radiation therapy is 10-15 months in patients with "limited" disease, and 7-11 months in patients with "extensive" disease.

The association between lung cancer and cigarette smoke is well established; however, other environmental factors also play a role in the etiology of lung cancer. One of these environmental agents is radon-222, a noble gas that is ubiquitous in the natural environment and is created by the decay of radium, which is in turn derived from the decay of uranium. Uranium is present in the earth's crust throughout the world. Radon gas forms within the earth's surface during uranium decay and diffuses into the atmosphere, where it becomes a health hazard. When radon decays in the atmosphere, its short-lived radioactive daughters (isotopes of polonium, bismuth, and lead) attach themselves to dust particles in the air. These radioactive particles as well as unattached radon daughters are then inhaled into the lungs. Radon and radon daughters give off alpha, beta, and gamma radiation. It is estimated that radon daughters deliver over 95% of the alpha radiation dose to the basal cells in the tracheobronchial epithelium of the lung.

Epidemiologic evidence has determined that exposure to radon and its daughters results in an increased risk of bronchial carcinoma. In the early 1960's, cytological techniques were developed to detect lung cancer in uranium miners, who, through multiple processes, are exposed to significant radon and radon daughter inhalation applied to the bronchial epithelium over a period of many years. It has been demonstrated further that the incidence of lung cancer in miners who smoke cigarettes is ten times greater than miners who did not smoke. These pulmonary cytopathology techniques have proven to be a very sensitive procedure for detecting abnormal/cancerous cells in high risk populations, such as uranium miners; however, once neoplastic cells have been identified, the task of localizing the occult carcinoma in the lung can be difficult, and in many cases an impossible problem. Because most in situ lesions cannot be seen with the unaided eye, such lesions must be localized by selective bronchial brushing and blind spur biopsies. These diagnostic procedures require general anesthesia and at least 2-3 hours to perform. The location of such early neoplastic lesions is of significant importance for the treatment of lung cancer. It is believed by many that for the treatment of lung cancer to be successful, the treatment procedure must be started at an early stage of cancer development (in situ). To successfully detect these early malignant lung lesions, new compounds must be developed which can be used in routine clinical procedures to detect small lung lesions.

Porphyrins and, in particular, hematoporphyrin derivative have been known for many years to have a significant affinity for malignant cancer cells, and have been demonstrated to be useful as diagnostic markers. Tumor cells that have taken up hematoporphyrin fluoresce when illuminated with uv light. However, the specificity of uptake of the porphyrins used in the past has not been as complete as desirable; that is, there is a substantial background of fluorescence from noncancerous cells accompanying the fluorescence from the cells of interest. Hematoporphyrin derivative has been used more recently for the imaging of neoplastic invasion of the bladder in humans. The procedure involves endoscopic exploration of the suspected tumor site with instrumentation that will detect fluorescent emission arising from the excitation of porphyrins with 400 nm light.

Porphyrins have also been used in the diagnosis and localization of small radiologically occult lung tumors (D. A. Cortese et al., "Hematoporphyrin Derivative In The Detection And Localization Of Radiographically Occult Lung Cancer," Am. Rev. Respir Dis 126, 1087 (1982); H. Kato et al., "Early Detection Of Lung Cancer By Means Of Hematoporphyrin Derivative Fluorescence And Laser Photoradiation," Clin. Chest Med. 6, 237 (1985) In these studies, a photoelectric fluorescence detection system in combination with a conventional bronchoscope was used to identify and localize early squamous cell carcinomas in patients with normal chest radiographs. K. B. Patel et al., "Fluorescing Cells In Sputum After Parenteral HPD," in *Progress In Clinical And Biological Research*, Vol. 170, D. Doiron and C. Gomer, Eds.; "Porphyrin Localization And Treatment Of Tumors," pp. 521-530 (1984) have also demonstrated that malignant cells could be detected in sputum samples from lung cancer patients injected with hematoporphyrin derivative. In this study, malignant cells as well as some nonmalignant cells fluoresced up to 9 days following the intravenous injection of the porphyrin. The uptake of porphyrin in normal cells is not unusual because other tissues, such as embryonic and traumatized tissues have also been reported to localize hematoporphyrin derivative.

The localization of malignant lesions using the procedures described above is dependent upon the visual detection of the red fluorescent emission of the porphyrin. In most procedures, this is accomplished by scanning the lung with a bronchoscope adapted to emit light at a wavelength (400 nm) which will excite the porphyrin molecules. The limiting factor with this procedure is that it is time consuming and requires highly trained personnel to examine all areas of the lung for malignant lesions. Because the fluorescent emission from these small lesions is so weak and difficult to observe, small lesions can easily be missed. In addition, to visually detect porphyrin fluorescence, the porphyrin must be on the surface of the tumor and the tumor must lie on the surface of the lung. Any material, such as mucous covering, or the situation where a tumor is deep-seated, interferes with the overlying detection of porphyrin fluorescence. As a result, porphyrins have not been used successfully as a diagnostic tool for occult lung lesions.

Accordingly, it is an object of our invention is to provide a method for selective irradiation of occult malignant tumor masses in the lungs of patients.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for treating lung cancer hereof includes introducing a sample of the $^{67}Cu$ complex of tetra-aryl porphyrin and, in particular, 5,10,15,20-tetrakis(4-carboxyphenyl)porphinato into the patient to be treated. Note that according to usual chemical terminology, free-base porphyrins are termed "porphines," while complexed porphyrins bear the "porphinato" label.

Benefits and advantages of the present invention include efficient, expeditious and economical identification of lung cancer cells in sputum samples and in biopsies, by bronchoscopic investigation of lungs, and by gamma ray imaging or positron emission tomography, as well as the site-selective ionizing radiation treatment of lung cancer masses without having to apply surgical techniques.

BRIEF DESCRIPTION OF THE DRAWINGS

The accompanying FIGURE, which is incorporated in and forms a part of the specification, illustrates an embodiment of the present invention and, together with the description, serves to explain the principles of the invention.

The FIGURE represents the structural formula for 5,10,15,20-tetrakis(4-carboxyphenyl)porphine (A), and that for the complex of this porphyrin and $^{67}Cu$ (B).

DETAILED DESCRIPTION OF THE PREFERRED EMBODIMENTS OF THE INVENTION

Briefly, the present invention includes the use of tetra-aryl porphyrins and, in particular, 5,10,15,20-tetrakis(4-carboxyphenyl)porphine (TCPP) as a fluorescent tracer for lung cancer cells, and as a radiotracer therefor as a complex with $^{67}Cu$. The latter complex also provides a source of beta radiation for selective destruction of lung malignancies as well as gamma radiation useful for image analysis of the situs thereof by single photon emission computed tomography, for example. $^{67}Cu$ may be substituted for the $^{67}Cu$ if only radiotracer characteristics are of interest. The copper-64 isotope of copper is a positron emitter, and well-known positron emission tomography techniques can be used to locate the malignant tissue mass. These uses derive from the affinity which TCPP and those from the same family of porphyrins have for lung malignancies when introduced into the vicinity of such cells.

Reference will now be made in detail to the present preferred embodiments of the invention, an example of which is illustrated in the accompanying Figure.

The FIGURE represents the structural formula for one example of a class of tetra-aryl porphyrins which may be used to practice the present invention, 5,10,15,20-tetrakis(4-carboxyphenyl)porphine, TCPP, (A), and that for the complex of this porphyrin and $^{67}Cu$ (B). A first investigation was conducted to determine whether TCPP would localize in neoplastic sputum cells obtained from uranium miners, and under what conditions would this process be maximized. A second study examined the localization of TCPP in different types of lung cancer cells (squamous cell, small cell, metastatic lung lymphoma, and adenocarcinoma), and the ability to diagnose lung cancer in such patients using TCPP.

A. Localization Of TCPP In Neoplastic Sputum Cells

Five parameters were investigated for this study: (1) the effect of various sputum processing procedures on the uptake of porphyrin in sputum cells, (2) the comparison of TCPP to three other porphyrins that are known for their uptake by tumors, (3) the time required for optimal uptake of the porphyrin in sputum cells, (4) the uptake of porphyrin in test and control sputum samples, and (5) the verification that TCPP was localizing in malignant sputum cells. In each of these investigations, the uptake of porphyrin in sputum cells was evaluated with a fluorescent microscope. Nonmetallated porphyrin fluoresces at approximately 650 nm. Sputum samples were evaluated for (1) the number of cells in the sputum samples which fluoresced, and (2) the intensity of the porphyrin fluorescence.

Processing Procedures:

Sputum samples require processing in order to produce a single cell suspension of lung cells. Sputum samples from test and control patients were collected and processed with alcohol and carbowax, alcohol only, phosphate-buffered saline (PBS), or left unprocessed. All samples were mixed with a blender for 1 minute following the addition of the processing mixture and then placed into petri dishes containing various porphyrins. Sputum samples processed with alcohol and carbowax or alcohol (no carbowax) had a larger number of cells free of the mucous than samples processed with PBS or unprocessed samples. Cells in the unprocessed sputum samples remained attached to the bottom of the petri dish with only a few cells free of the mucous. Sputum samples processed with PBS had the greatest number of live cells when compared to sputum samples processed with alcohol or alcohol/carbowax; however, sputum cells processed with alcohol or alcohol/carbowax had the highest TCPP uptake, suggesting that TCPP may have an affinity for nonviable processed cells.

(2) Evaluation Of Different Porphyrins:

Four porphyrins selected for their known affinity for neoplastic cells were tested for their ability to detect malignant sputum cells. Sputum cells obtained from each of the four processing procedures set forth above were treated with one of hematoporphyrin derivative, HPD, 5,10,15,20-tetrakis(4-carboxyphenyl)porphine, TCPP, 5,10,15,20-tetrakis(4-sulfonatophenyl)porphine, TTPS, or uroporphyrin, URO. In all investigations, the porphyrins were dissolved in tissue culture medium at a concentration of 200 µg/ml. Following the addition of porphyrin, each sample was incubated at 37° C. for a specific length of time.

Following the incubation period, each sputum sample was examined for porphyrin uptake with a fluorescent microscope. The background fluorescence from porphyrin uptake by nonmalignant cells was lower in some measurements. Sputum samples which had been incubated with TCPP had the greatest number of cells fluorescing and the greatest contrast (brightness) between fluorescing malignant cells and background fluorescence, indicating significant porphyrin uptake in the malignant bodies. Sputum samples processed with HPD and TPPS had moderate porphyrin uptake, and samples processed with URO had the least porphyrin uptake.

3. Incubation Time:

Each sputum sample was incubated at 37° C. with each of the porphyrins for either 6 or 24 hours and then evaluated for porphyrin uptake with a fluorescent microscope. At the 6 hour incubation period, the cells had begun to localize porphyrin; however, when the sputum cells were washed with PBS, the fluorescence diminished considerably. This suggests that the porphyrin was not firmly bonded or internalyzed into the cells. By 24 hours, by contrast, the uptake of porphyrin by sputum cells increased considerably. This was demonstrated by the number of cells which had taken up porphyrin and the intensity of porphyrin fluorescence. When the sputum cells that had been incubated for 24 hours were washed with PBS, the porphyrin remained attached to the cells. Longer incubation times were not investigated.

4. Uptake In Test And Control Samples:

Control sputum samples did not contain neoplastic cells. However, a large number of inflammatory cells were found to be present. When porphyrin uptake in the test and control samples were compared (i.e., the number of sputum cells which fluoresced), the porphyrin uptake in the control samples was considerably lower than the uptake in the test samples. In addition, the fluorescence intensity of the few control cells that did fluoresce was lower than the fluorescence intensity of the test cells. The most dramatic difference between the uptake of porphyrin by test and control sputum cells was seen in samples incubated with TCPP.

5. Identification Of Sputum Cells Which Fluoresced:

To assist in the identification of the neoplastic cells, sputum samples which had the greatest TCPP uptake were stained with PAP stain, a stain routinely used by cytologists to identify neoplastic cells. Cells identified as neoplastic using the PAP stain were marked and re-examined for TCPP uptake with a fluorescent microscope. Although the fluorescence intensity of the TCPP had been reduced by the PAP staining procedure, TCPP fluorescence was seen in every neoplastic cell.

B. Localization Of TCPP In Different Types Of Lung Cancers

Studies were conducted using patients having confirmed squamous cell lung carcinoma, oat cell lung carcinoma, lung adenocarcinoma, and advanced metastatic lymphoma (lung metastasis) using procedures identical to those set forth above. Using as a measure the number of fluorescent cells in a sputum sample times the fluorescence intensity of the cells, it was found that this number was 3–6 times greater for sputum samples from cancer patients than for noncancerous patients. These studies also confirm that TCPP and carbowax and ethanol resulted in the greatest uptake of porphyrin in neoplastic sputum cells.

Further investigations determined that TCPP also localizes in cancers of the lung grown in tissue cultures. Moreover, squamous carcinoma cells grown in culture and treated with TCPP can easily be detected using flow cytometry, and autofluorescence of control cells (cells not exposed to TCPP) was negligible when compared to the fluorescence of cells exposed to TCPP. Expanding the investigations to other types of lung cells, it was found that human small cell (oat cell) lung carcinoma absorbed TCPP in 2–3 times lower quantities than did the squamous cell line, but this is still considerably higher than uptake in normal cells. It was also found that normal human lung epithelial cells concentrated TCPP at only slightly above autofluorescence or background levels; that is, at many times lower concentration than that TCPP concentration in the neoplastic cell lines examined. Incubating the cells for 24 hours in TCPP was more than adequate to maximize the TCPP localization, and fixing the cells prior to TCPP exposure increased the TCPP uptake. Paraformaldehyde as a fixant was found to slightly increase the TCPP uptake of the cells over those fixed with alcohol and carbowax.

C. Supportive Investigations Using $^{67}$Cu

1. Production of Copper-67 and Copper-67/Porphyrin Complex:

The production of copper-67 involves the irradiation of a zinc oxide target with 600 to 800 MeV protons for several days. The spallation reaction in the target produces not only $^{67}$Cu, but also several other isotopes of lighter mass than zinc. The purification procedure is complicated and involves the separation of $^{67}$Cu from zinc and other metals by electrochemical plating (J. A. Mercer-Smith et al., "The Development Of Copper-67 Labeled Porphyrin-Antibody Conjugates," in *Targeted Diagnosis And Therapy*, Vol. 1, Antibody-Mediated Delivery Systems; J. T. Rodwell, Ed. (Marcel Dekker, New York, 1988) pp.317–352). Preparation of $^{67}$CuTCPP is achieved from either N-bzHTCPP or TCPP by radiometallation with $^{67}$CuCl$_2$.

2. Serum Stability of $^{67}$Cu TCPP:

An important consideration in the development of a radiopharmaceutical is the stability of the complex $^{67}$Cu TCPP to the loss of the radioisotope $^{67}$Cu in vivo. To test the stability of $^{67}$CuTCPP, a fluorescence method capitalizing on the fact that copper porphyrins do not fluoresce, while nonmetallated do, was developed by which the loss of copper could be measured under simulated physiological conditions (J. C. Roberts et al., "Preparation And Characterization Of Copper-$^{67}$ Porphyrin-Antibody Conjugates," J. Immunol. Methods 105, 153 (1987). It was found that the stability of CuTCPP in human serum albumin, and two chelating agents, EDTA and DTPA was such that less than one percent conversion (the limit of detection) occurred in incubation periods of up to 12 days. In addition, there was no detectable transcomplexation with other metal ions as indicated by ultraviolet-visible spectroscopy.

3. Biodistribution And Biological Half-Life Of $^{67}$CuTCPP:

A sterile dose of $^{67}$CuTCPP ($1.0 \times 10^{-6}$ gm) was intravenously injected into the tail vein of rats. It was determined that the liver and kidney of these normal animals (no cancer) were the major organs of $^{67}$CuTCPP localization. From these results, it can be concluded that $^{67}$CuTCPP is suitable for detection and treatment of cancerous lung tissue in vivo, since normal lung tissue does not appear to take up significant quantities of $^{67}$CuTCPP, making lung tumor to normal lung cell uptake ratios substantial. A biological half-life study demonstrated that $^{67}$CuTCPP is biologically eliminated from the animals following a normal exponential decay curve, with a half-life of 108 hours.

The foregoing description of several preferred embodiments of the invention has been presented for purposes of illustration and description. It is not intended to be exhaustive or to limit the invention to the precise form disclosed, and obviously many modifications and variations are possible in light of the above teaching. For example, it would be apparent to one having ordinary skill in the art of cancer detection and treatment after studying the present disclosure that a method for locating the situs of lung malignancies in vivo, could include injecting a sample of the $^{64}$Cu complex of 5,10,15,20-tetrakis(4-carboxyphenyl)porphinato into the bloodstream, or directing an aerosol containing this complex into the lungs of a patient to be diagnosed, and performing positron emission tomography (G. Firnau et al., "$^{64}$Cu Labelling Of Hematoporphyrin Derivative For Non-Invasive In-Vivo Measurements Of Tumour Uptake," in *Progress In Clinical And Biological Research*, vol. 170, D. Doiron and C. Gomer, eds.; "Porphyrin Localization And Treatment Of Tumors," pp. 629–636 (1984)). For radioisotope labeling using isotopes having long half-lives, it would be apparent to an individual having such skill in the relevant art that it would also be effective to introduce the $^{64}$Cu complexes into tissue for subsequent diffusion into the bloodstream. It would further be apparent to a practitioner having ordinary skill that samples could be prepared from biopsies of tissue masses as well as from sputum samples for in vitro diagnoses.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for treating lung cancer, comprising the step of injecting a sample of the $^{67}$Cu complex of 5,10,15,20-tetrakis(4-carboxyphenyl)porphinato into the bloodstream of a patient to be treated in an effective amount.

2. A method for treating lung cancer, comprising the step of directing an aerosol containing the $^{67}$Cu complex of 5,10,15,20-tetrakis(4-carboxyphenyl)porphinato into the lungs of a patient to be treated in an effective amount.

* * * * *